United States Patent
Kikuchi et al.

(10) Patent No.: US 8,129,573 B2
(45) Date of Patent: Mar. 6, 2012

(54) METHOD FOR PURIFYING FERMENTATION ALCOHOL

(75) Inventors: Masao Kikuchi, Tokyo (JP); Shunsuke Nakanishi, Yamaguchi (JP)

(73) Assignee: UBE Industries, Ltd., Ube-shi (JP)

( * ) Notice: Subject to any disclaimer, the term of this patent is extended or adjusted under 35 U.S.C. 154(b) by 23 days.

(21) Appl. No.: 12/920,039

(22) PCT Filed: Mar. 2, 2009

(86) PCT No.: PCT/JP2009/053901
§ 371 (c)(1),
(2), (4) Date: Sep. 22, 2010

(87) PCT Pub. No.: WO2009/107840
PCT Pub. Date: Sep. 3, 2009

(65) Prior Publication Data
US 2011/0009677 A1    Jan. 13, 2011

(30) Foreign Application Priority Data

Feb. 29, 2008  (JP) .................... 2008-050584
Mar. 31, 2008  (JP) .................... 2008-092425

(51) Int. Cl.
*C07C 29/80* (2006.01)
*C07C 29/82* (2006.01)
(52) U.S. Cl. ......... 568/913; 568/918; 568/920; 568/921
(58) Field of Classification Search .......... 568/913, 568/918, 920, 921
See application file for complete search history.

(56) References Cited

U.S. PATENT DOCUMENTS

| 2002/0035922 A1 | 3/2002 | Nakanishi et al. |
| 2006/0070867 A1 | 4/2006 | Ikeda et al. |

FOREIGN PATENT DOCUMENTS

| JP | A-S62-32871 | 2/1987 |
| JP | A-S63-258602 | 10/1988 |
| JP | A-H02-184388 | 7/1990 |
| JP | A-2000-342901 | 12/2000 |
| JP | A-2001-269553 | 10/2001 |
| JP | A-2002-345495 | 12/2002 |
| WO | WO 2004/073841 | 9/2004 |

OTHER PUBLICATIONS

International Search Report issued in corresponding PCT Application No. PCT/JP2009/053901, mailed Jun. 2, 2009.
International Preliminary Report on Patentability and Written Opinion in corresponding PCT Application No. PCT/JP2009/053901, mailed Oct. 21, 2010.
Kagaku Kogakukai Dai 57, Mar. 2, 1992, p. 12, B 315.

*Primary Examiner* — Elvis O Price
(74) *Attorney, Agent, or Firm* — Knobbe Martens Olson & Bear LLP

(57) ABSTRACT

The present invention relates to a method for purifying an aqueous solution of fermentation alcohol to give anhydrous alcohol, wherein a mash column is controlled such a manner that an alcohol concentration of an alcohol/water mixed vapor distilled from a mash column is less than 50% by weight and a reflux amount of a condensate to a distillation column is controlled such a manner that an alcohol concentration of an alcohol/water mixed vapor that is distilled from the distillation column is 65 to 85% by weight. According to the present method, the purification for obtaining an anhydrous alcohol from an aqueous solution of a fermentation alcohol with the use of a mash column, a distillation column, an evaporator and a membrane separator can be more conveniently carried out with an extremely high energy efficiency as the whole process.

5 Claims, 2 Drawing Sheets

METHOD FOR PURIFYING FERMENTATION ALCOHOL

This application is the U.S. National Phase under 35 U.S.C. §371 of International Application PCT/JP2009/053901, filed Mar. 2, 2009, designating the U.S., and published in Japanese as WO2009/107840 on Sep. 3, 2009, which claims priority to Japanese Patent Application No. 2008-050584, filed Feb. 29, 2008; and to Japanese Patent Application No. 2008-092425, filed Mar. 31, 2008, the entire contents of which are incorporated herein by reference.

TECHNICAL FIELD

The present invention relates to a method for purifying fermentation alcohol; particularly, a method for purifying fermentation alcohol using a mash column, a distillation column, an evaporator and a membrane separator in combination, whereby fermentation alcohol can be more conveniently purified with a very high energy efficiency.

BACKGROUND ART

As a method for purifying fermentation alcohol liquid discharged from a fermenter, a conventional method is separating and concentrating an alcohol-water mixture from the fermentation alcohol liquid (mash) by a mash column; further concentrating the alcohol-water mixture substantially to an azeotropic composition by a concentrating column; and then treating it by an azeotropic distillation column to give high-purity anhydrous alcohol.

Patent Reference No. 1 has disclosed a method using a membrane separator in place of an azeotropic distillation column, wherein an alcohol-water mixture concentrated substantially to an azeotropic composition by a distillation column is evaporated in an evaporator and introduced to the membrane separator to be purified.

Patent Reference No. 2 has also disclosed the identical system to that in Patent Reference No. 1. On the system disclosed in the reference, when a distillate from a distillation column is heated by introducing into an evaporator, an alcohol/water mixed vapor with a higher pressure than an operating pressure of the distillation column is generated, and the high-pressure vapor is introduced to a membrane separator, so that the membrane separator can be very efficiently operated. The reference has described that the distillation column is operated such a manner that 10 to 90% of a condensate obtained by condensing the distillate discharged from the top of the distillation column is refluxed to the distillation column, but has not described preferable operating conditions in view of an energy efficiency. In Examples therein, 10% by weight of an ethanol aqueous solution is concentrated to 80% by weight by feeding to a distillation column, and the condensate is evaporated in an evaporator and fed to a membrane separator.

Citation List
Patent Literature

Patent Reference No. 1: Japanese Laid open publication No. S63-258602.

Patent Reference No. 2: WO 2004/073841.

SUMMARY OF INVENTION

Technical Problem

By using a membrane separator in place of an azeotropic distillation column, a facility can be simplified and an energy efficiency can be improved. However, there has not been sufficiently investigated specific approach to more conveniently purify fermentation alcohol with extremely high energy efficiency as a whole process in a method for purifying a fermentation alcohol using a mash column, a distillation column, an evaporator and a membrane separator in combination.

Specifically, an objective of the present invention is to provide a more convenient method for purifying an aqueous solution of fermentation alcohol to give anhydrous alcohol with extremely high energy efficiency as a whole process having steps of feeding an aqueous solution of fermentation alcohol to a mash column, distilling a distillate containing an alcohol/water mixed vapor by heating an aqueous solution of fermentation alcohol in the mash column, and feeding the distillate containing the mixed vapor from the mash column or a first condensate obtained by condensing the distillate to a distillation column; distilling the alcohol/water mixed vapor from the distillation column by heating the distillate or the first condensate, refluxing a part of a second condensate obtained by condensing the mixed vapor to the distillation column, and feeding the remaining part of the second condensate to an evaporator; and then, generating an alcohol/water mixed vapor by heating the condensate in the evaporator, feeding the alcohol/water mixed vapor to a membrane separator, and selectively removing water vapor from the alcohol/water mixed vapor.

Solution to Problem

The present invention relates to the followings.

[1] A method for purifying an aqueous solution of fermentation alcohol to give anhydrous alcohol, comprising:

(step 1) feeding an aqueous solution of fermentation alcohol to a mash column, distilling a distillate containing an alcohol/water mixed vapor by heating an aqueous solution of fermentation alcohol in the mash column, and feeding the distillate from the mash column containing the mixed vapor or a first condensate obtained by condensing the distillate into a distillation column;

(step 2) distilling an alcohol/water mixed vapor from the distillation column by heating the distillate or the first condensate, refluxing a part of a second condensate obtained by condensing the mixed vapor to the distillation column and feeding the remaining part of the second condensate to an evaporator; and then, (step 3) generating an alcohol/water mixed vapor by heating the second condensate in the evaporator and feeding this alcohol/water mixed vapor to a membrane separator, and selectively removing water vapor from the alcohol/water mixed vapor, wherein the mash column is controlled such a manner that an alcohol concentration of the alcohol/water mixed vapor distilled from the mash column in step 1 (of course, a concentration or more of the aqueous solution of fermentation alcohol) is less than 50% by weight, preferably 12% by weight or more and less than 50% by weight, more preferably 20% by weight or more and less than 50% by weight, further preferably 30% by weight or more and less than 50% by weight, and a reflux amount of the condensate to the distillation column is controlled such a manner that an alcohol concentration of the alcohol/water mixed vapor distilled by the distillation column in step 2 is 65 to 85% by weight, preferably 65 to 78% by weight.

[2] The method for purifying an aqueous solution of fermentation alcohol to give anhydrous alcohol as described in [1], wherein in steps 1 and 2, each operating pressure in mash column and distillation column is 50 to 150 kPa (absolute pressure), preferably an atmospheric pressure, and in step 3, an operating pressure of the evaporator is 150 kPa (absolute pressure) or more, preferably 200 kPa (absolute pressure) or more.

[3] The method for purifying an aqueous solution of fermentation alcohol to give anhydrous alcohol according to [1] or [2], wherein in step 2, an alcohol/water mixed vapor is distilled from the distillation column by heating the distillate fed from the mash column or the first condensate, and less than 50%, preferably less than 35%, more preferably less than 20%, particularly preferably less than 10% of the second condensate obtained by condensing the mixed vapor is refluxed to the distillation column.

[4] The method for purifying an aqueous solution of fermentation alcohol to give anhydrous alcohol according to any of [1] to [3], wherein the bottom liquid in the distillation column in step 2 is recycled to the mash column in step 1, and the membrane-permeated component in the membrane separator in step 3 is condensed to be a condensate and then recycled to the distillation column in step 2.

[5] The method for purifying an aqueous solution of fermentation alcohol to give anhydrous alcohol according to any of [1] to [4], wherein an aqueous solution of fermentation alcohol is neutralized by adding an alkaline component before being fed to the mash column.

Advantageous Effects of Invention

According to the present invention, it is provided a more convenient method for purifying an aqueous solution of fermentation alcohol to give anhydrous alcohol with extremely high energy efficiency as a whole process having the steps of feeding an aqueous solution of fermentation alcohol to a mash column, distilling a distillate containing an alcohol/water mixed vapor by heating an aqueous solution of fermentation alcohol in the mash column, and feeding this distillate or a first condensate obtained by condensing the distillate to a distillation column; distilling an alcohol/water mixed vapor from the distillation column by heating the first condensate, refluxing a part of a second condensate obtained by condensing the mixed vapor to the distillation column, and feeding the remaining part of the condensate to an evaporator; and then, generating an alcohol/water mixed vapor by heating the second condensate in the evaporator, feeding the alcohol/water mixed vapor to a membrane separator, and selectively removing water vapor from the alcohol/water mixed vapor.

DESCRIPTION OF EMBODIMENTS

FIG. 1 schematically shows an example of an embodiment according to the present invention. There will be described a method for purifying an aqueous solution of fermentation alcohol to give anhydrous alcohol of the present invention with reference to FIG. 1. However, the present invention is not limited to this embodiment. In the present invention, anhydrous alcohol means alcohol having a purity of 99.0% by weight or more, preferably 99.5% by weight or more, more preferably 99.7% by weight or more, particularly preferably 99.8% by weight or more.

In the present invention, while the term "alcohol" may include lower-alkyl alcohols such as methyl alcohol, propyl alcohol and butyl alcohol, it is preferably ethanol.

In the present invention, there are no particular restrictions to an aqueous solution of fermentation alcohol. For example, it may be an aqueous solution of fermentation alcohol obtained by fermenting saccharine materials, starch ones and/or cellulose ones. These materials are fermented in a fermenter to give an aqueous solution of fermentation alcohol. An alcohol concentration of the aqueous solution of fermentation alcohol is generally about 5 to 12% by weight. This aqueous solution of fermentation alcohol contains, in addition to water and the alcohol as main components, yeasts and bacteria, and various byproducts including alcohols such as methanol, fatty acids such as formic acid, acetic acid, succinic acid, lactic acid and butyric acid, aldehydes such as acetaldehyde and formaldehyde, esters such as ethyl acetate and butyl acetate, acetals such as diethyl acetal, ketones such as acetone and methyl ethyl ketone, amines such as pyridine, picoline, 3-methylamine and 4-methylpyridine, and a mixture of higher alcohols and higher fatty acid esters, so-called fusel oil. In general, unfermented materials remain as insoluble component, giving a slurry.

This aqueous solution of fermentation alcohol is fed to the mash column 10 directly from the fermenter or indirectly after it is stored in a tank. It is preferable that the aqueous solution of fermentation alcohol is treated by coarse filtration to remove large insolubles before being fed to the mash column. Furthermore, the aqueous solution of fermentation alcohol after fermentation in the fermenter may have a pH of about 3 to 5 due to fatty acids as byproducts. Thus, it is preferable to neutralize the acid components contained in the aqueous solution of fermentation alcohol by, for example, adding an alkaline component. Such neutralization is preferable because contamination of anhydrous alcohol with acids after purification can be reliably prevented. Suitable examples of an alkaline component added include water-soluble alkali compounds such as sodium hydroxide, potassium hydroxide and potassium permanganate.

In the mash column 10, the aqueous solution of fermentation alcohol is heated to distill a distillate containing an alcohol/water mixed vapor, and a condensate obtained by condensing the distillate is fed to the distillation column 20. The distillate containing the mixture of an alcohol and water is preferably an alcohol/water mixed vapor (gas state), and may be a mixture of an alcohol/water mixed vapor and droplets of the aqueous solution of fermentation alcohol and the like (mixing gas-liquid state).

In the present invention, a main function of the mash column 10 is separation and removal of insoluble components including the unfermented material and high-boiling components such as fusel oil preferably together with low-boiling byproducts and/or water from the aqueous solution of fermentation alcohol while discharge of the alcohol to outside from the system (i.e. loss) is reduced as much as possible. There are no particular restrictions to the mash column as long as the above function is achieved, and a conventional known type column can be suitably used. It may be either a simple distillation type or a continuous distillation type. The number of distillation plates is suitably several; for example, a tray type such as a mountain-shaped cap type tray or a baffle type tray with less scale adhesion can be suitably used. Furthermore, it may be a simple distillation type such as a flash distillation or a combination of two or more such types. An operating pressure of the mash column is preferably a reduced pressure or an atmospheric pressure.

As shown in FIG. 1, the aqueous solution of fermentation alcohol as a material is introduced from a supply port relatively near the top of the mash column 10 into the column. Meanwhile, water vapor (steam) is blown from an inlet near the column bottom. The water vapor moves upwards in the column while exchanging heat and materials with a liquid falling in the column. Thus, vapor components in the column bottom are substantially converted into water and an alcohol concentration of the vapor in the vicinity of the top of the column is increased. As a result, from the column bottom, water containing little alcohol is discharged as a bottom liquid together with insoluble components. Here, instead of introducing water vapor from the column bottom, a part of the bottom liquid discharged from the column bottom may be vaporized by a reboiler and then introduced into the column.

The distillate containing the alcohol/water mixed vapor discharged from the column top or the concentration plate in the mash column 10 is fed to the condenser 11 and then condensed. A part of the condensate is refluxed to the mash column and the remaining part of the condensate is fed to the distillation column 20. By adjusting a proportion of refluxed condensate to the mash column 10, a concentration of an alcohol in the distillate fed from the mash column 10 to the distillation column 20 can be controlled.

Although not being the aspect shown in FIG. 1, the distillate containing an alcohol/water mixed vapor discharged from the column top or the concentration plate of the mash column 10 can be fed to the distillation column 20 as a gas or a mixture of gas and liquid without being condensed. In this aspect, but not limited to, a part of the distillate containing an alcohol/water mixed vapor may be fed to the distillation column 20, the remaining part of the distillate may be condensed by a condenser to give a condensate, and all of the condensate is refluxed into the mash column. Here, depending on a ratio of the distillate fed to the condenser, an alcohol concentration in the distillate fed from the mash column 10 to the distillation column 20 is controlled.

When the alcohol/water mixed vapor contains a significant amount of low-boiling components such as an aldehyde which may adversely affect the separation membrane in the membrane separator 40, it is suitable, for protecting the separation membrane, that the distillate discharged from the column top of the mash column 10 is partially condensed (a part of low-boiling components are partially left in a vapor and the remaining part of the alcohol/water mixed vapor is condensed) to separate the low-boiling components such as an aldehyde from the alcohol/water mixed vapor and to remove them outside the system.

In the present invention, an alcohol concentration in the distillate fed from the mash column 10 to the distillation column 20 is controlled to be less than 50% by weight, preferably 12% by weight or more and less than 50% by weight, more preferably 20% by weight or more and less than 50% by weight, further preferably 30% by weight or more and less than 50% by weight (of course, which is equal to or more than the alcohol concentration of the aqueous solution of fermentation alcohol) for improving an energy efficiency in the whole process from the mash column to the membrane separator. By concentrating the alcohol concentration to some extent in the mash column, an energy consumption required for heating/vaporization in the distillation column 20 can be reduced. However, if the concentration of 50% by weight or more is sought, the mash column is excessively expected to further concentrate alcohol, in addition to the function described above (to separate and remove insoluble components including the unfermented material or high-boiling components such as fusel oil preferably together with low-boiling byproducts and/or water while discharge of the alcohol is reduced as much as possible), and therefore, it becomes necessary to add a further concentration plate above the supply port of an aqueous solution of fermentation alcohol in the mash column 10, which inevitably leads to a larger and more complicated apparatus.

When an aqueous solution of fermentation alcohol containing insoluble components (not completely removed by coarse filtration) or high-boiling components is fed to such a larger and more complicated mash column, the insoluble components or the high-boiling components entrained in the vapor are carried to the concentration plate and may cause problems such as deposition as a scale, making it difficult to stably operate the mash column with a high energy efficiency.

An alcohol concentration in the distillate fed to the distillation column 20 is controlled to be less than 50% by weight, preferably 12% by weight or more and less than 50% by weight, more preferably 20% by weight or more and less than 50% by weight, further preferably 30% by weight or more and less than 50% by weight (of course, which is equal to or more than the alcohol concentration of the aqueous solution of fermentation alcohol) because it can be easily achieved by a convenient apparatus with about several distillation plates or less and even when an alcohol/water mixed vapor is condensed and refluxed to the mash column, a proportion of reflux can be considerably reduced, resulting in high-speed treatment and reduced energy consumption.

When the alcohol/water mixed vapor is condensed and refluxed to the mash column, a higher proportion of reflux causes reduction in a treated amount of the mash per unit operation; in other words, an energy consumption per an unit amount of alcohol increases, leading to a reduced energy efficiency as a whole process.

A proportion of refluxed condensate in the mash column is preferably 20% or less, more preferably 10% or less.

The role of the distillation column 20 in the present invention is concentrating the distillate from the mash column to an alcohol/water mixed vapor with an alcohol concentration of 65 to 85% by weight, preferably 65 to 78% by weight at an operating pressure of 50 to 150 kPa, preferably an atmospheric pressure.

This alcohol/water mixed vapor with an alcohol concentration of 65 to 85% by weight, preferably 65 to 78% by weight is fed as a condensate to the evaporator 30 and after being vaporized in the evaporator 30, fed to the membrane separator 40, where it is purified to anhydrous alcohol.

If the vapor is concentrated in the distillation column 20 to an alcohol concentration of less than 65% by weight, it is undesirable because an energy consumption in the evaporator in the subsequent step is increased, so that the fermentation alcohol cannot be more conveniently purified into anhydrous alcohol with an extremely higher energy efficiency as a whole process. On the other hand, if the vapor is concentrated to an alcohol concentration of more than 85% by weight (for example, near the azeotropic composition) in the distillation column 20, it is undesirable because the fermentation alcohol cannot be more conveniently purified into anhydrous alcohol with an extremely higher energy efficiency as a whole process.

The distillation column 20 may be of any type including a tray type and a packed tower as long as it is suitable for general distillation operation. In the middle of the distillation column, there is disposed a feeding part for feeding the distillate or a condensate of the distillate from the mash column. A part of the bottom liquid is heated by the reboiler 21 to become vapor, which moves upwards in the column while exchanging heat and materials with a liquid falling in the column. A mixed vapor of alcohol and water distilled from the column top or the concentration plate is concentrated to an alcohol concentration of 65% by weight or more, preferably 70% by weight or more and 85% by weight or less, preferably 80% by weight or less, more preferably 78% by weight or less, and then fed to the condenser. The bottom liquid in the distillation column 20 may contain alcohol to be collected and suitably recycled to the mash column 10.

An operating pressure of the distillation column 20 is preferably within 50 to 150 kPa (absolute pressure), and generally an atmospheric pressure. An operating pressure of more than 150 kPa (absolute pressure) is undesirable because a construction cost for the distillation column is increased and a heating temperature is increased, which increases an energy consumption. An operating pressure of less than 50 kPa (absolute pressure) is undesirable because a condensation temperature of the mixed vapor of alcohol and water distilled from the column top or the concentration plate is lowered, resulting in increase in an energy consumption in the condenser.

The reboiler 21 for heating the bottom liquid in the distillation column 20 may utilize condensation heat of steam supplied from the outside, but condensation heat of non-permeated vapor in the membrane separator 40 can be suitably utilized, for example, as preheating.

The condenser 22 cools the mixed vapor of alcohol and water distilled from the column top or the concentration plate to give a condensate. The condensate may be temporarily stored in the condensate tank 23. A part of the condensate is refluxed to the column top or the concentration plate by, for example, a pump for condensate, and the remaining part of the condensate is fed to the evaporator 30. Depending on a proportion of refluxed condensate to the distillation column 20, an alcohol concentration in the alcohol/water mixed vapor obtained in the column top or the concentration plate of the distillation column can be suitably controlled. In the present invention, a proportion of refluxed condensate to the distillation column 20 is controlled to adjust an alcohol concentration in the alcohol/water mixed vapor obtained in the column top or the concentration plate in the distillation column 20 within the range of 65 to 85% by weight.

When a proportion of reflux is increased, a treated amount in the distillation column 20 is decreased and a treated speed is reduced, which causes a reduction in an efficiency such as increase in an energy consumption, and therefore, a proportion of refluxed condensate is preferably relatively lower. Preferably, it is less than 50%, more preferably less than 35%, further preferably less than 20%, particularly preferably less than 10% of the condensate.

Condensation heat of the condenser 22 can be utilized as preheating for the distillate fed to the distillation column. The distillate fed is preferably pre-heated to near its boiling point. Here, vapor which is not condensed in the condenser 22 is preferably condensed by cooling water in an auxiliary condenser.

In the present invention, an aqueous solution of alcohol with an alcohol concentration of 65 to 85% by weight is fed to the evaporator 30 from the distillation column 20 via the condenser 22. The function of the evaporator 30 is that the aqueous solution of alcohol is heated to be completely vaporized and is then fed to the membrane separator 40 as an alcohol/water mixed vapor. The evaporator 30 suitably has adequate heating ability to allow for processing the mixed vapor of alcohol and water obtained at a relatively higher pressure of 100 kPa (absolute pressure) or more, preferably 120 kPa (absolute pressure) or more, more preferably 200 kPa (absolute pressure) or more. The upper limit of the pressure is about 700 kPa (absolute pressure) or less.

The whole amount of the alcohol/water mixed vapor obtained in the evaporator 30 is fed to the membrane separator 40 and then the purification is conducted. For preventing the mixed vapor from being condensed during this process, it is suitably superheated by a superheater to a temperature higher by about 5° C. or more before being fed to the membrane separator. Here, an operating pressure of the evaporator 30 can be suitably controlled by adjusting (controlling) a flow rate of the vapor flowing the non-permeate side in the membrane separator 40. Furthermore, a pressure in the evaporator 30 is preferably regulated such a manner that an evaporation temperature in the evaporator 30 is higher than a temperature of the column bottom in the distillation column 20 by about 5° C. or more. Thus, non-permeated vapor in the membrane separator 40 can be utilized as a heat source for the reboiler in the distillation column 20.

In the present invention, an aqueous alcohol solution having a relatively lower alcohol concentration of 65 to 85% by weight is fed to the evaporator as the result of simplification of separation/purification in the distillation column. Thus, the condensate fed to the evaporator may be contaminated with a trace amount of impurities such as so-called fusel oil which are contained in the aqueous solution of fermentation alcohol. In such a case, continuous operation may cause problems such as bumping due to the impurities accumulated in the evaporator. It is, therefore, preferable in the present invention to remove the accumulated impurities by discharging a part of the bottom liquid in the evaporator continuously or intermittently while operation.

In the membrane separator 40, the alcohol/water mixed vapor flows in contact with a selective permeable separation membrane. Here, since water vapor selectively permeates the separation membrane, mixed vapor with a reduced alcohol concentration mainly comprised of water vapor is collected in the permeate side of the separation membrane. An alcohol concentration in this mixed vapor is about several to several ten % by weight (for example, 20% by weight of alcohol), and for improving a recovery rate of alcohol, the vapor is suitably recycled to the distillation column 20 (as a condensate after condensation, or as a stripping vapor as it is). On the other hand, in the non-permeate side of the separation membrane, water vapor is removed, so that a high-purity anhydrous alcohol can be collected.

Generally, an amount of water vapor permeated through the separation membrane is proportional to a difference in a partial pressure of water vapor each side of the membrane. Thus, in the present invention, it is suitable to generate an alcohol/water mixed vapor with a relatively high pressure of about 100 kPa (absolute pressure) or more, preferably 120 to 700 kPa (absolute pressure) in the evaporator 30 and then to feed it to the membrane separator. It is also suitable to simultaneously reduce the pressure of the permeate side of the separation membrane. Specifically, the space in the permeate side of the separation membrane is connected to a vacuum pump 42 via a heat exchanger (condenser) 41 whereby the space is vacuumed, and the permeated vapor after permeated through the separation membrane is condensed in the condenser to give a condensate. This condensate is preferably stored in a condensate tank 43 and then recycled to the distillation column 20.

There are no particular restrictions to the membrane separator 40 as long as it can separate water vapor from a mixed vapor of water vapor and ethanol vapor in a separation membrane. Furthermore, there are also no particular restrictions to a separation membrane as long as it can selectively permeate water vapor to alcohol vapor. The membrane may be made of a polymer such as polyimides, polyetherimides, polycarbonates, polysulfones and high-molecular-weight polyvinyl alcohols, or an inorganic material such as zeolite and zirconia. In terms of the type of the membrane separator, conventional well-known types can be suitably used, such as a shell-and-tube type module equipped a hollow-fiber separation membrane module consisting of an asymmetric polyimide hollow-fiber membrane or equipped with a tubular separation membrane element in which zeolite is deposited on a porous tubular support. Examples can be, but not limited to, those using a polyimide hollow-fiber membrane as described in Japanese laid open publication Nos. 2000-262838 and 2001-

62257 and those using a zeolite membrane as described in Japanese laid open publication Nos. 2003-93844, 2006-263574 and 2007-203210.

In terms of permeation performance of a separation membrane, in use, the membrane suitably has a water-vapor permeation rate ($P'_{H2O}$) of preferably $0.5 \times 10^{-3}$ cm$^3$ (STP)/cm$^2$·sec·cmHg or more, more preferably $1.0 \times 10^{-3}$ cm$^3$ (STP)/cm$^2$·sec·cmHg or more, and a ratio of a water-vapor permeation rate ($P'_{H2O}$) to an alcohol permeation rate ($P'_{alcohol}$)($P'_{H2O}/P'_{alcohol}$) of preferably 50 or more, more preferably 100 or more.

FIG. 2 schematically shows another example of an embodiment according to the present invention.

Specifically, the bottom liquid discharged from the mash column 10 is used for pre-heating an aqueous solution of fermentation alcohol fed to the mash column 10, and non-permeated vapor (anhydrous alcohol vapor) in the membrane separator 40 is used for pre-heating a reboiler in the distillation column 20 and for pre-heating during recycling a condensate of permeated vapor in the membrane separator 40 to the distillation column 20.

EXAMPLES

There will be further detailed the present invention with reference to Examples, but the present invention is not limited to them.

Example 1

We tried to purify an aqueous solution of fermentation ethanol having an ethanol concentration of 7.3% by weight prepared in a fermenter at a flow rate of 72.7 t/hr using an apparatus which is schematically illustrated in FIG. 2, to give anhydrous ethanol with a purity of 99.8% by weight at a flow rate of 5 t/hr.

Step 1

An aqueous solution of fermentation ethanol having an ethanol concentration of 7.3% by weight is pre-heated by a pre-heater, and fed to a mash column having a number of theoretical plates of about 5 by a feed pump at a flow rate of 72.7 t/hr. Water vapor (steam 1) required for distillation by evaporating the aqueous solution of fermentation ethanol fed is directly introduced to the column bottom of the mash column. The mixed vapor of ethanol and water distilled in the mash column and discharged from the column top is completely condensed in a condenser. A part of the condensate is refluxed to the mash column and the remaining part of the condensate is fed to a distillation column. Here, a reflux amount is adjusted such a manner that an ethanol concentration in the column top of the mash column is 39% by weight.

Step 2

An aqueous solution of ethanol having an ethanol concentration of 39% by weight at a flow rate of 16.4 t/hr by a feed pump is fed to a distillation column having a number of theoretical plates of about 4. The column bottom in the distillation column is equipped with a reboiler. A bottom liquid discharged from the column bottom is preheated by non-permeated vapor (anhydrous ethanol vapor) in the membrane separator, and converted to a mixed vapor by a reboiler having an adequate heat transfer area and circulating volume where a required amount of steam 2 is supplied. Then the mixed vapor is recycled to the distillation column. Simultaneously, the bottom liquid discharged from the column bottom is recycled to the mash column at a flow rate of 8.3 t/hr. In the bottom liquid, an ethanol concentration is kept at about 2.5% by weight or less.

The ethanol/water mixed vapor distilled in the distillation column and discharged from the column top is completely condensed in the condenser. A part of the condensate is refluxed to the distillation column and the remaining part of the condensate is fed to the evaporator. A reflux amount is adjusted such a manner that an ethanol concentration in the column top of the distillation column is 70% by weight. A flow rate of the condensate fed to the evaporator is 8.1 t/hr.

Step 3

The condensate (an aqueous solution of ethanol having an ethanol concentration of 70% by weight) fed to the evaporator is heated by steam 3, to be completely converted to a mixed vapor of ethanol and water with an ethanol concentration of 70% by weight at a pressure of 300 kPa (gauge pressure), and then superheated to 135° C. by a superheater (steam 3) and fed to the membrane separator.

The membrane separator is a module as described in Japanese laid open publication No. 2000-262838, in which there are 27 pieces of a module with an effective membrane area of 125 m$^2$ including a polyimide asymmetric hollow-fiber separation membrane having an outer diameter of 500 μm and an inner diameter of 310 μm in which a water vapor permeation rate ($P'_{H2O}$) at 135° C. is $1.2 \times 10^{-3}$ cm$^3$ (STP)/cm$^2$·sec·cmHg and a ratio of a water vapor permeation rate ($P'_{H2O}$) to an ethanol permeation rate ($P'_{EtOH}$) ($P'_{H2O}/P'_{EtOH}$) is 143.

The permeate side of the membrane separator is equipped with a vacuum pump via a condenser, and a vapor permeated through the separation membrane is completely condensed in the condenser to keep a vacuum degree in the permeate side of the separation membrane. Furthermore, a part of the non-permeated vapor discharged from the membrane separator is fed to the permeate side of the membrane separator as a purge gas for improving a separation efficiency of the membrane separator.

After the vapor in the permeate side of the separation membrane in the membrane separator (the permeated vapor and the vapor fed as a purge gas) is completely condensed, it is preheated by non-permeated vapor and recycled to the distillation column. Furthermore, the non-permeated vapor collected from the non-permeate side of the separation membrane in the membrane separator is, after heat recovery in the preheating described above, cooled and collected in a product tank at a flow rate of 5 t/hr as anhydrous ethanol having an ethanol concentration of 99.8% by weight.

When 99.8% by weight anhydrous ethanol is produced by such a process, a calorie required for producing 1 kg of 99.8% by weight anhydrous ethanol was converted from the total amount of steam used in the whole process (steam 1 to 4). The results are shown in Table 1.

Examples 2 and 3

While modifying the conditions as shown in Table 1, we tried to purify a 7.3% by weight aqueous solution of fermentation ethanol as described in Example 1 at a flow rate of 72.7 t/hr to produce 99.8% by weight anhydrous ethanol at a flow rate of 5 t/hr. The results are shown in Table Comparative Examples 1 and 2

While modifying the conditions as shown in Table 1, we tried to purify a 7.3% by weight aqueous solution of fermentation ethanol as described in Examples at a flow rate of 72.7 t/hr to produce 99.8% by weight anhydrous ethanol at a flow rate of 5 t/hr. The results are shown in Table 1.

TABLE 1

|  | Example 1 | Example 2 | Example 3 | Comparative Example 1 | Comparative Example 2 |
|---|---|---|---|---|---|
| Aqueous solution of fermentation ethanol (wt %) | | | | | |
| Ethanol concentration (wt %) | 7.3 | 7.3 | 7.3 | 7.3 | 7.3 |
| Feeding rate (treated rate, t/hr) | 72.7 | 72.7 | 72.7 | 72.7 | 72.7 |
| Mash column | | | | | |
| Number of theoretical plates | 5 | 5 | 5 | 5 | 5 |
| Proportion of refluxed condensate (%) | 7.4 | 7.4 | 7.4 | 7.4 | 7.4 |
| Ethanol concentration in a column top (wt %) | 39 | 39 | 39 | 39 | 39 |
| Distillation column | | | | | |
| Number of theoretical plates | 4 | 6 | 6 | 4 | 21 |
| Proportion of refluxed condensate (%) | 2 | 4 | 31 | 2 | 63 |
| Ethanol concentration in a column top (wt %) | 70 | 75 | 80 | 60 | 90 |
| Membrane separator | | | | | |
| Required membrane area ($m^2$) | 3431 | 3193 | 2946 | 3916 | 2332 |
| Required module number | 27 | 26 | 24 | 31 | 19 |
| Anhydrous ethanol after purification | | | | | |
| Ethanol concentration (wt %) | 99.8 | 99.8 | 99.8 | 99.8 | 99.8 |
| Production rate (t/hr) | 5.0 | 5.0 | 5.0 | 5.0 | 5.0 |
| Energy consumption per 1 kg of ethanol throughout the whole process from an mash column to a membrane separator (MJ/1 kg of ethanol) | 7.23 | 7.02 | 7.60 | 7.84 | 8.57 |

As shown in Table 1, in Examples 1 to 3, both distillation column and membrane separator are simple, and fermentation alcohol can be purified with an extremely higher energy efficiency. In Comparative Example 1, an energy efficiency is lower and a large separation membrane apparatus is required. In Comparative Example 2, a proportion of refluxed condensate in the distillation column is larger, so that an energy efficiency is lowered and a large distillation column is required.

Industrial Applicability

The present invention can provide a more convenient method for purifying an aqueous solution of fermentation alcohol to give anhydrous alcohol with extremely high energy efficiency as a whole process having the steps of feeding an aqueous solution of fermentation alcohol to an mash column, distilling a distillate containing an alcohol/water mixed vapor by heating an aqueous solution of fermentation alcohol in the mash column, and feeding the distillate or a first condensate obtained by condensing the distillate to a distillation column; distilling the alcohol/water mixed vapor from the distillation column by heating the distillate fed from the mash column or the first condensate in the distillation column, refluxing a part of a second condensate obtained by condensing the mixed vapor to the distillation column, and feeding the remaining part of the second condensate to an evaporator; and then, generating an alcohol/water mixed vapor by heating the second condensate in the evaporator and feeding the alcohol/water mixed vapor to a membrane separator, and selectively removing water vapor from the alcohol/water mixed vapor.

Figure 1:
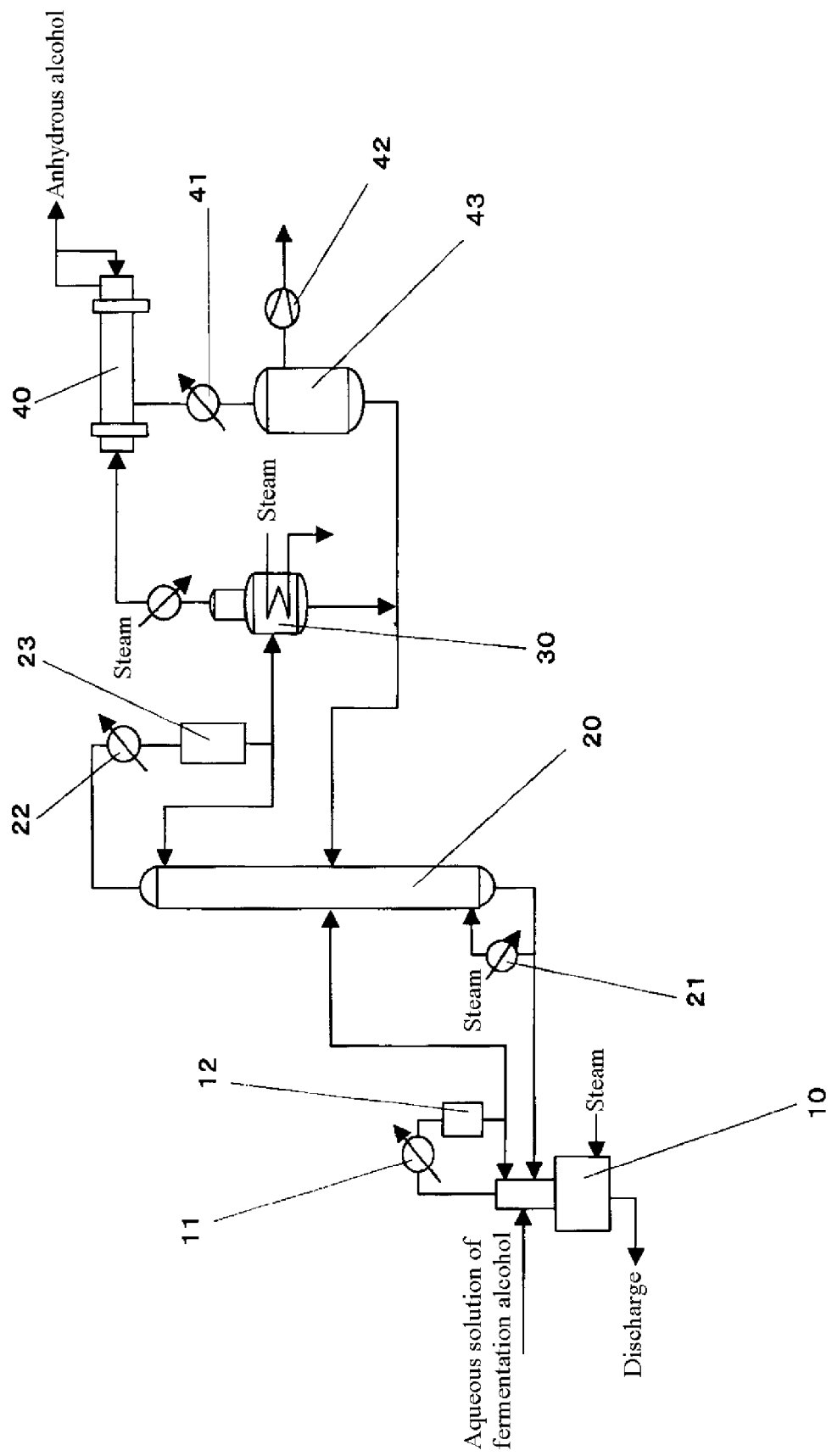
FIG. 1 is a diagrammatic illustration (block diagram) schematically showing an example of an embodiment according to a method for purifying an aqueous solution of fermentation alcohol to give anhydrous alcohol of the present invention.
Figure 2:
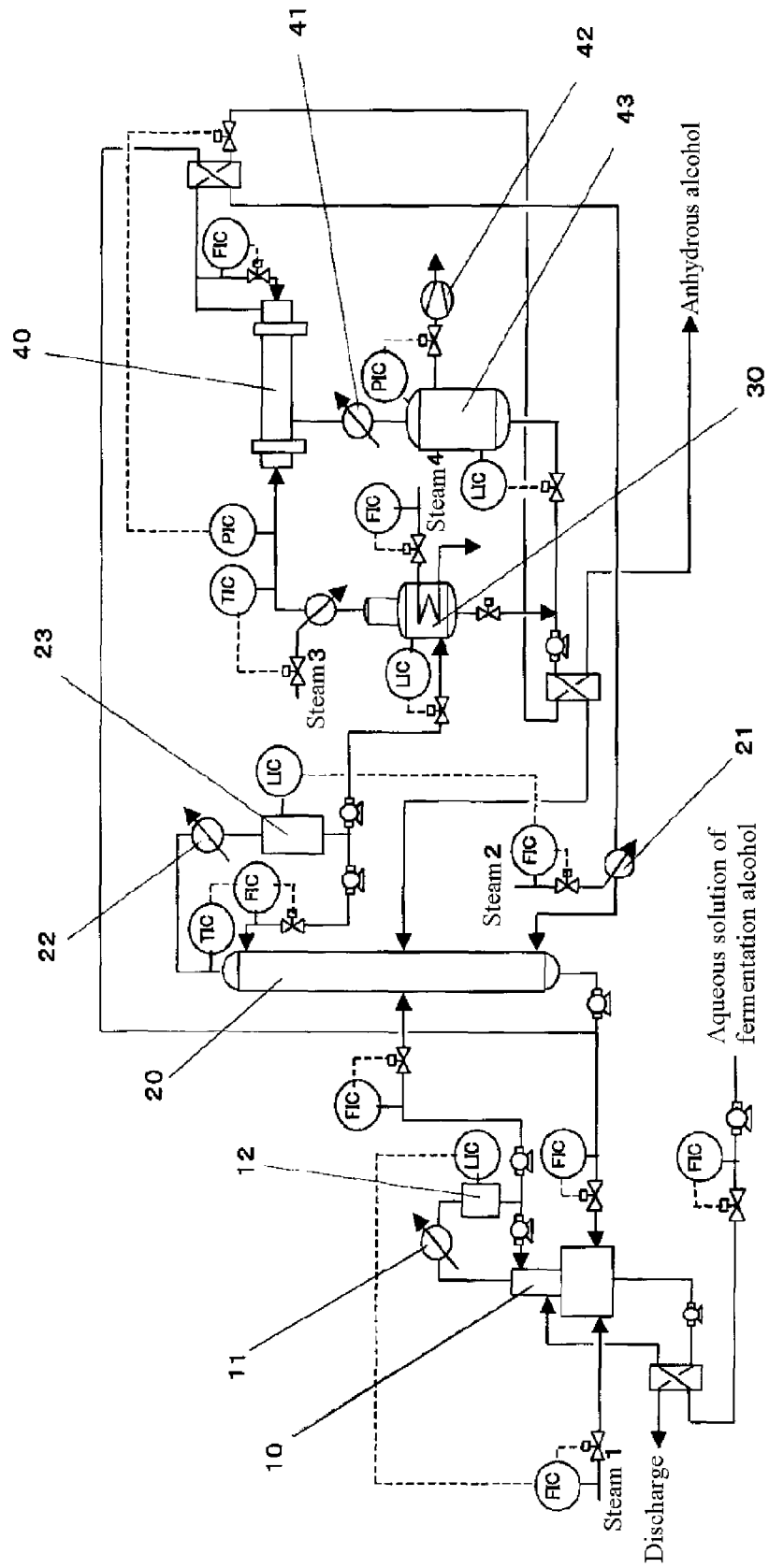
FIG. 2 is a diagrammatic illustration (block diagram) schematically showing another example of an embodiment according to a method for purifying an aqueous solution of fermentation alcohol to give anhydrous alcohol of the present invention (block diagram).

In the drawings, a solid line indicates flow of a liquid or gas (vapor) and a dotted line indicates connection in a control system.

In the drawings, the symbols denote the following meanings; 10: mash column, 11: condenser, 12: condensate tank, 20: distillation column, 21: reboiler, 22: condenser, 23: condensate tank, 30: evaporator, 40: membrane separator, 41: heat exchanger (condenser), 42: vacuum pump, 43: condensate tank, FIC: flow indication controller, LIC: level indication controller, TIC: temperature indication controller, and PIC: pressure indication controller.

The invention claimed is:

1. A method for purifying an aqueous solution of fermentation alcohol to give anhydrous alcohol, comprising:
   (step 1) feeding an aqueous solution of fermentation alcohol to a mash column,
   distilling a distillate containing an alcohol/water mixed vapor by heating an aqueous solution of fermentation alcohol in the mash column, and
   feeding the distillate or a first condensate obtained by condensing the distillate into a distillation column;
   (step 2) distilling an alcohol/water mixed vapor from the distillation column by heating the distillate or the first condensate,
   refluxing a part of a second condensate obtained by condensing the mixed vapor to the distillation column, and
   feeding the remaining part of the second condensate to an evaporator; and then,
   (step 3) generating an alcohol/water mixed vapor by heating the second condensate in the evaporator, feeding the alcohol/water mixed vapor to a membrane separator, and selectively removing the water vapor from the alcohol/water mixed vapor, wherein the mash column is controlled in such a manner that an alcohol concentration of the alcohol/water mixed vapor distilled from the mash column in step 1 is less than 50% by weight, and a reflux amount of the condensate to the distillation column is controlled in such a manner that an alcohol concentration of the alcohol/water mixed vapor distilled from the distillation column in step 2 is 65 to 85% by weight.

2. The method for purifying an aqueous solution of fermentation alcohol to give anhydrous alcohol according to claim 1, wherein in steps 1 and 2, each operating pressure in mash column and distillation column is 50 to 150 kPa (absolute pressure) and in step 3, an operating pressure of the evaporator is 150 kPa (absolute pressure) or more.

3. The method for purifying an aqueous solution of fermentation alcohol to give anhydrous alcohol according to claims 1 or 2, wherein in step 2, an alcohol/water mixed vapor is distilled from the distillation column by heating the distillate fed from the mash column or the first condensate, and less than 50% of the second condensate obtained by condensing the mixed vapor is refluxed to the distillation column.

4. The method for purifying an aqueous solution of fermentation alcohol to give anhydrous alcohol according to claim 3, wherein the bottom liquid in the distillation column in step 2 is recycled to the mash column in step 1, and the membrane-permeated component in the membrane separator in step 3 is condensed to be a condensate and then recycled to the distillation column in step 2.

5. The method for purifying an aqueous solution of fermentation alcohol to give anhydrous alcohol according to claim 3, wherein an aqueous solution of fermentation alcohol is neutralized by adding an alkaline component before being fed to the mash column.

* * * * *